US00PP35615P3

(12) United States Plant Patent
Hopmans

(10) Patent No.: US PP35,615 P3
(45) Date of Patent: Jan. 30, 2024

(54) ***HEBE* PLANT NAMED 'HOP104'**

(50) Latin Name: ***Hebe* Comm. ex. Juss.**
Varietal Denomination: HOP104

(71) Applicant: FIRMA E. HOPMANS, Wieringerwerf (NL)

(72) Inventor: Rudolf Johannes Hopmans, Wieringerwerf (NL)

(73) Assignee: FIRMA E. HOPMANS V.O.F., Wieringerwerf (NL)

( * ) Notice: Subject to any disclaimer, the term of this patent is extended or adjusted under 35 U.S.C. 154(b) by 0 days.

(21) Appl. No.: 18/199,070

(22) Filed: May 18, 2023

(65) Prior Publication Data

US 2023/0380311 P1 Nov. 23, 2023

Related U.S. Application Data

(60) Provisional application No. 63/344,425, filed on May 20, 2022.

(51) Int. Cl.
*A01H 5/02* (2018.01)
*A01H 6/68* (2018.01)

(52) U.S. Cl.
USPC ..... Plt./251

(58) Field of Classification Search
USPC ..... Plt./251, 226, 263.1
CPC ..... A01H 5/02; A01H 5/00; A01H 6/68
See application file for complete search history.

(56) References Cited

U.S. PATENT DOCUMENTS

PP34,496 P3 * 8/2022 Hopmans ..... A01H 6/68
Plt./226

* cited by examiner

*Primary Examiner* — June Hwu
(74) *Attorney, Agent, or Firm* — C. Anne Whealy

(57) ABSTRACT

A new and distinct cultivar of *Hebe* plant named 'HOP104', characterized by its compact and upright to outwardly spreading and uniformly mounding plant habit; freely branching habit; dark green-colored leaves; freely flowering habit with numerous purple-colored flowers that resist fading; and long flowering period.

1 Drawing Sheet

Botanical designation: *Hebe* Comm. ex. Juss.
Cultivar denomination: 'HOP104'.

An European Community Plant Breeder's Rights application for the instant plant was filed by the Applicant/Assignee, Firma E. Hopmans of Wieringerwerf, The Netherlands on Apr. 20, 2021, application number 2021/1071. Foreign priority is not claimed to this application.

BACKGROUND OF THE INVENTION

The present invention relates to a new and distinct cultivar of *Hebe* plant, botanically known as *Hebe* Comm. ex. Juss., typically grown as a potted plant and hereinafter referred to by the name 'HOP104'.

The new *Hebe* plant is a product of a planned breeding program conducted by the Inventor in Wieringerwerf, The Netherlands. The objective of the breeding program is to develop new compact *Hebe* plants with attractive flowers that resist fading.

The new *Hebe* plant originated from a cross-pollination in April, 2016 in Wieringerwerf, The Netherlands of a proprietary selection of *Hebe* Comm. ex. Juss. identified as code number 146A, not patented, as the female, or seed, parent with a proprietary selection of *Hebe* Comm. ex. Juss. identified as code number 212, not patented, as the male, or pollen, parent. The new *Hebe* plant was discovered and selected by the Inventor as a single flowering plant from within the progeny of the stated cross-pollination grown in a controlled greenhouse environment in Wieringerwerf, The Netherlands in October, 2016.

Asexual reproduction of the new *Hebe* plant by terminal stem cuttings in a controlled environment in Wieringerwerf, The Netherlands since February, 2017 has shown that the unique features of this new *Hebe* plant are stable and reproduced true to type in successive generations.

SUMMARY OF THE INVENTION

Plants of the new *Hebe* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'HOP104'. These characteristics in combination distinguish 'HOP104' as a new and distinct *Hebe* plant:

1. Compact and upright to outwardly spreading and uniformly mounding plant habit.
2. Freely branching habit.
3. Dark green-colored leaves.
4. Freely flowering habit with numerous purple-colored flowers that resist fading.
5. Long flowering period.

Plants of the new *Hebe* differ primarily from plants of the female parent selection in flower color as plants of the new *Hebe* have purple-colored flowers whereas plants of the female parent selection have pink-colored flowers. In addition, plants of the new *Hebe* have smaller leaves than plants of the female parent selection.

Plants of the new *Hebe* differ primarily from plants of the male parent selection in plant habit as plants of the new *Hebe* are not as compact as plants of the male parent selection. In addition, plants of the new *Hebe* have longer inflorescences than plants of the male parent selection.

Plants of the new *Hebe* can be compared to plants of *Hebe* Comm. ex. Juss. 'Zakita', not patented. In side-by-side comparisons, plants of the new *Hebe* differ primarily from plants of 'Zakita' in inflorescence length as plants of the new *Hebe* have shorter inflorescences than plants of 'Zakita'. In addition, plants of the new *Hebe* are more compact than plants of 'Zakita'.

BRIEF DESCRIPTION OF THE PHOTOGRAPH

The accompanying colored photograph illustrates the overall appearance of the *Hebe* plant showing the colors as true as it is reasonably possible to obtain in colored reproductions of this type. Colors in the photograph may differ slightly from the color values cited in the detailed botanical description which accurately describe the actual colors of the new *Hebe* plant. The photograph is a side perspective view of a typical flowering plant of 'HOP104' grown in a container.

DETAILED BOTANICAL DESCRIPTION

Plants used for the aforementioned photograph and following description were grown in 13-cm containers during the summer and early autumn in a glass-covered greenhouse in Wieringerwerf, The Netherlands and under cultural practices typical of commercial *Hebe* production. During the production of the plants, day temperatures ranged from 16C to 20C and night temperatures ranged from 12C to 16C. Plants were pinched one time about one month after planting and were five months old when the photograph and the description were taken. In the following description, color references are made to The Royal Horticultural Society Colour Chart, 2015 Edition, except where general terms of ordinary dictionary significance are used.

Botanical classification: *Hebe* Comm. ex. Juss. 'HOP104'.

Parentage:

- *Female, or seed, parent.*—Proprietary selection of *Hebe* Comm. ex. Juss. identified as code number 146A, not patented.
- *Male, or pollen, parent.*—Proprietary selection of *Hebe* Comm. ex. Juss. identified as code number 212, not patented.

Propagation:

- *Type cutting.*—Terminal stern cuttings.
- *Time to initiate roots, summer.*—About ten days at temperatures about 18C.
- *Time to initiate roots, winter.*—About 14 days at temperatures about 20C.
- *Time to produce a rooted young plant, summer.*—About 40 days at temperatures about 18C.
- *Time to produce a rooted young plant, winter.*—About 50 days at temperatures about 20C.
- *Root description.*—Medium in thickness, fleshy; typically white to brown in color, actual color of the roots is dependent on substrate composition, water quality, fertilizer type and formulation, substrate temperature and physiological age of roots.
- *Rooting habit.*—Moderately freely branching; medium density.

Plant description:

- *Plant type.*—Evergreen perennial shrub.
- *Plant and growth habit.*—Compact and upright to outwardly spreading and uniformily mounding plant habit; vigorous growth habit and moderate to rapid growth rate.
- *Plant height, soil level to top of foliar plane.*—About 23.3 cm.
- *Plant height, soil level to top of floral plane.*—About 24.1 cm.
- *Plant width.*—About 36.7 cm.
- *Lateral branch description.*—Branching habit: Freely branching habit with about eight primary branches, each with about nine secondary branches; pinching enhances lateral branching potential. Length (excluding inflorescence): About 9.8 cm. Diameter: About 3 mm. Internode length: About 1.7 cm. Strength: Strong. Aspect: Erect to about 60 degrees from vertical. Texture and luster: Mostly smooth and glabrous; at the internodes, moderately pubescent; slightly glossy. Color, developing: Close to 144B. Color, developed: Close to 146C; at the internodes, close to 176A.

Leaf description:

- *Arrangement.*—Opposite, simple.
- *Length.*—About 5.5 cm.
- *Width.*—About 2 cm.
- *Shape.*—Elliptic to oblong; occasionally, slightly obovate.
- *Apex.*—Apiculate with a bluntly acute tip to bluntly acute.
- *Base.*—Cuneate.
- *Margin.*—Entire; slightly revolute and slightly and coarsely undulate; not lobed.
- *Texture and luster, upper surface.*—Smooth, glabrous; not rugose; moderately glossy.
- *Texture and luster, lower surface.*—Smooth, glabrous; not rugose; slightly glossy.
- *Venation pattern.*—Pinnate.
- *Color.*—Developing leaves, upper surface: Close to NN137B. Developing leaves, lower surface: Close to 138B; towards the margins, slightly tinged with close to 176B; midvein, close to 148B. Fully expanded leaves, upper surface: Slightly darker than 147A; venation, close to 147B. Fully expanded leaves, lower surface: Close 147B; venation, close to a blend of 147B and 147C.
- *Petioles.*—Length: About 2 mm. Diameter: About 2 mm by 4.5 mm. Strength: Strong. Texture and luster, upper and lower surfaces: Smooth, glabrous; slightly glossy. Color, upper surface: Close to 145A tinged with close to 177D to lighter than 177D. Color, lower surface: Close to 145A.

Flower description:

- *Flower arrangement and shape.*—Single campanulate flowers arranged on dense axillary racemes; flowers face mostly outwardly.
- *Flowering habit.*—Freely flowering habit with about 130 flowers developing per inflorescence and about 15,000 flowers developing per plant during the flowering season.
- *Fragrance.*—None detected.

*Natural flowering season.*—Plants begin flowering about 140 days after planting; plants flower continuously from the summer into the autumn in The Netherlands.

*Flower longevity.*—Flowers last about one week on the plant; flowers not persistent.

*Flower buds.*—Length: About 6 mm. Diameter: About 2 mm. Shape: Oblong. Texture and luster: Smooth, glabrous; matte. Color: Developing sepals, close to 138A; developing petals, close to a blend of N87A and N88A.

*Inflorescence height* (*length*).—About 7.5 cm.

*Inflorescence diameter.*—About 3.2 cm.

*Flower diameter.*—About 7 mm by 7 mm.

*Flower height.*—About 1 cm.

*Throat diameter.*—About 1.5 mm.

*Tube length.*—About 3 mm.

*Tube diameter.*—About 2.25 mm.

*Petals.*—Quantity and arrangement: Four arranged in a single whorl; petals fused about 42.5% of the petal length from the base. Length: About 7 mm. Width: About 2.5 mm. Shape: Narrowly obovate to narrowly oblong; moderately concave. Apex, upper petal: Obtuse. Apex, lateral and lower petals: Bluntly acute. Margin: Entire; moderately involute; not undulate. Texture and luster, upper and lower surfaces: Smooth, glabrous; slightly glossy. Texture and luster, throat and tube: Smooth, glabrous; slightly glossy. Color: When opening, upper surface: Close to N87A. When opening, lower surface: Close to N87A; distally, close to N87B. Fully opened, upper surface: Close to a blend of N87A and N88A; venation, close to a blend of N87A and N88A; color does not change with subsequent development. Fully opened, lower surface: Close to N87A; venation, close to N87A; color does not change with subsequent development. Throat: Close to N87A; venation, close to N87A. Tube: Close to a N87A and N87B; venation, close N87A and N87B.

*Sepals.*—Quantity and arrangement: Four arranged in a single whorl and fused at the base. Length: About 3 mm. Width: About 1.25 mm. Shape: Narrowly ovate. Apex: Acute. Base: Cuneate, fused. Margin: Entire. Texture and luster, upper and lower surfaces: Smooth, glabrous; matte. Color: When opening, upper surface: Close to 143A. When opening, lower surface: Close to 143A tinged with close to 72A. Fully opened, upper surface: Close to 137D. Fully opened, lower surface: Close to 137D tinged with close to 72B.

*Peduncles.*—Length: About 9.3 cm. Diameter: About 2 mm. Aspect: About 45 degrees from stem axis. Strength: Strong. Texture and luster: Densely pubescent; slightly glossy. Color: Close to 144B.

*Pedicels.*—Length: About 3 mm. Diameter: About 0.5 mm. Aspect: About 85 degrees from peduncle axis. Strength: Moderately strong. Texture and luster: Densely pubescent; matte. Color: Close to 138B.

*Flower bracts.*—Quantity and arrangement: One at the base of each flower. Length: About 2.5 mm. Width: About 1 mm. Shape: Narrowly ovate. Apex: Acute. Base: Cuneate. Margin: Entire. Texture, upper and lower surfaces: Smooth, glabrous. Color, upper and lower surfaces: Close to 137D.

*Reproductive organs.*—Stamens: Quantity per flower: Two. Filament length: About 8.5 mm. Filament color: Close to 86A. Anther size: About 0.75 mm by 2 mm. Anther shape: Oblong. Anther color: Close to 83B. Pollen amount: Moderate. Pollen color: Close to 11D. Pistils: Quantity per flower: One. Pistil length: About 8.5 mm. Stigma diameter: About 5 mm. Stigma shape: Club-shaped. Stigma color: Greyish white. Style length: About 8.45 mm. Style color: Close to 86A. Ovary color: Close to 143C.

*Seeds and fruits.*—To date, seed and fruit development has not been observed on plants of the new *Hebe*.

Pathogen & pest resistance: To date, plants of the new *Hebe* have not been noted to be resistant to pathogens and pests common to *Hebe* plants.

Garden performance: Plants of the new *Hebe* have exhibited good garden performance and to be tolerant to rain, wind, temperatures ranging from about −7C to about 40C and to be suitable for USDA Hardiness Zones 8 to 11.

It is claimed:

1. A new and distinct *Hebe* plant named 'HOP104' as illustrated and described.

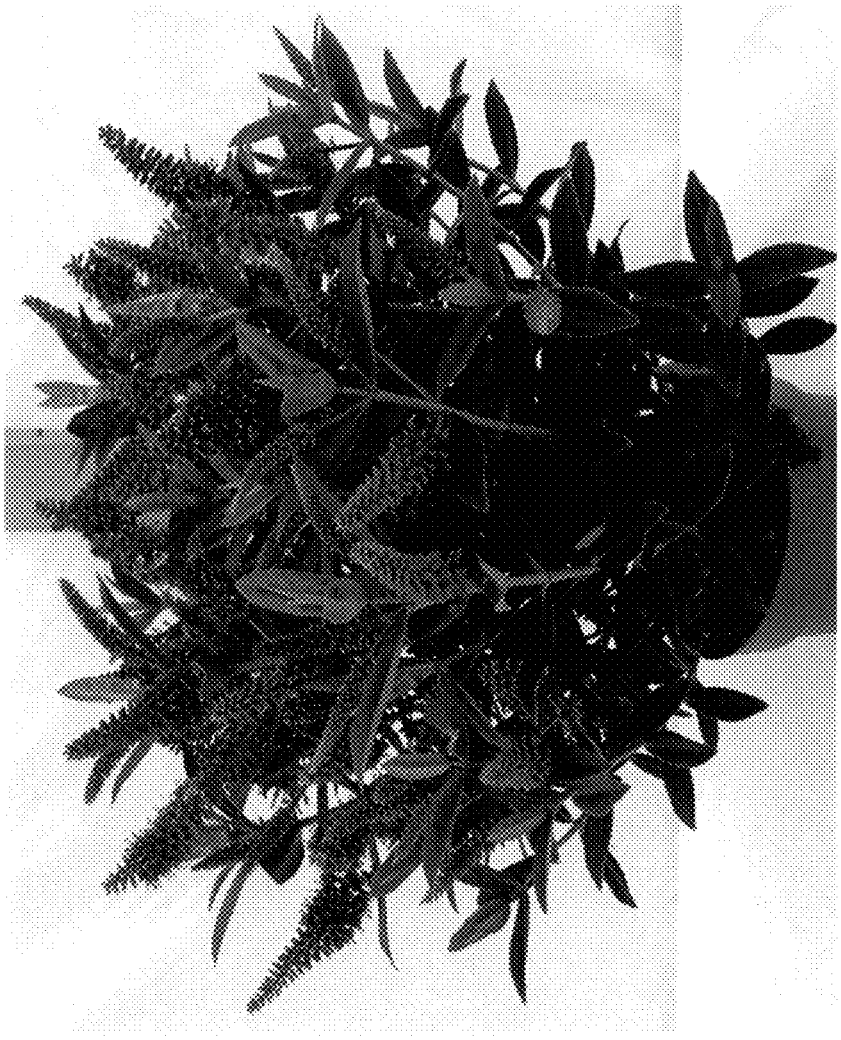

* * * * *